(12) United States Patent
Nakajima et al.

(10) Patent No.: US 7,492,447 B2
(45) Date of Patent: Feb. 17, 2009

(54) REFRACTOMETER

(75) Inventors: Yoshinori Nakajima, Saitama (JP);
Hideyuki Amamiya, Saitama (JP);
Masaki Osawa, Saitama (JP); Kiminori Sekiguchi, Higashimatsuyama (JP)

(73) Assignee: Atago Co., Ltd., Tokyo (JP)

( * ) Notice: Subject to any disclaimer, the term of this patent is extended or adjusted under 35 U.S.C. 154(b) by 448 days.

(21) Appl. No.: 10/693,904

(22) Filed: Oct. 28, 2003

(65) Prior Publication Data

US 2004/0145731 A1 Jul. 29, 2004

(30) Foreign Application Priority Data

Oct. 30, 2002 (JP) ............................. 2002-315814

(51) Int. Cl.
*G01N 21/41* (2006.01)

(52) U.S. Cl. ..................................... 356/128

(58) Field of Classification Search .......... 356/128–137
See application file for complete search history.

(56) References Cited

U.S. PATENT DOCUMENTS

| | | | |
|---|---|---|---|
| 3,311,014 A | 3/1967 | Witt et al. | |
| 3,540,808 A | 11/1970 | Harmon et al. | |
| 3,628,867 A | 12/1971 | Brady | |
| 4,469,441 A | 9/1984 | Bernier et al. | |
| 4,571,075 A | 2/1986 | Kamrat | |
| 4,640,616 A | 2/1987 | Michalik | |
| 4,704,029 A * | 11/1987 | Van Heuvelen | ............... 356/39 |
| 4,844,608 A | 7/1989 | Smith | |
| 5,548,393 A | 8/1996 | Nozawa et al. | |
| 6,067,151 A | 5/2000 | Salo | |
| 6,097,479 A | 8/2000 | Melendez et al. | |
| 6,172,746 B1 * | 1/2001 | Byrne et al. | ................ 356/135 |
| 6,447,167 B1 | 9/2002 | Kashiwada et al. | |
| 6,760,098 B2 * | 7/2004 | Salo | ............................ 356/135 |
| 6,816,248 B2 * | 11/2004 | Sharma et al. | .............. 356/136 |
| 7,030,989 B2 * | 4/2006 | Yager et al. | ................. 356/445 |

(Continued)

FOREIGN PATENT DOCUMENTS

DE    1936346    7/1970

(Continued)

OTHER PUBLICATIONS

English Language Abstract of JP 3-26443.

(Continued)

*Primary Examiner*—Hwa S Lee
(74) *Attorney, Agent, or Firm*—Greenblum & Bernstein, P.L.C.

(57) ABSTRACT

A refractometer for measuring refractive index of a sample comprising a prism having an interface contacting the sample, a light source that radiates light towards the interface from an entrance face of the prism, and a photoelectric sensor for receiving light reflected at the interface and directed outward from an exit face of the prism. The light source and the photoelectric sensor are secured to the prism. The refractometer comprises a sample stage arranged surrounding the interface surface. This sample stage provides a non-adhesive coating formed on the surface thereof. The refractometer comprises filter means arranged between the interface surface and the photoelectric sensor. This filter means includes a wavelength filter that selectively allows transmission of light having a wavelength within a prescribed region, including a wavelength of light of the light source.

13 Claims, 9 Drawing Sheets

U.S. PATENT DOCUMENTS

| | | | |
|---|---|---|---|
| 2002/0164096 | A1 | 11/2002 | Kashiwada et al. |
| 2003/0034454 | A1 | 2/2003 | Nomura et al. |

FOREIGN PATENT DOCUMENTS

| | | |
|---|---|---|
| DE | 2642891 | 3/1978 |
| DE | 1 9910301 | 9/2000 |
| EP | 0035081 | 9/1981 |
| EP | 0071143 | 2/1983 |
| EP | 0284270 | 9/1988 |
| EP | 0389446 | 9/1990 |
| FR | 2578978 | 9/1986 |
| GB | 257127 | 8/1926 |
| GB | 462332 | 3/1937 |
| GB | 2008793 | 6/1979 |
| GB | 2054845 | 2/1981 |
| JP | 8-114547 | 5/1976 |
| JP | 51124977 | 10/1976 |
| JP | 52-40187 | 3/1977 |
| JP | 63-033645 | 2/1988 |
| JP | 64-38634 | 2/1989 |
| JP | 1-202642 | 8/1989 |
| JP | 3-26443 | 6/1991 |
| JP | 5-172632 | 7/1993 |
| JP | 6-012949 | 2/1994 |
| JP | 6-021872 | 3/1994 |
| JP | 6-323990 | 11/1994 |
| JP | 9-281000 | 10/1997 |
| JP | 11-295214 | 10/1999 |
| JP | 2000-19110 | 1/2000 |
| JP | 2001-074647 A | 3/2001 |
| JP | 2001-200838 A | 7/2001 |
| JP | 2001-242079 A | 9/2001 |
| JP | 2003-057178 | 2/2003 |
| JP | 2003-215035 | 7/2003 |
| WO | 02/052249 | 7/2002 |

OTHER PUBLICATIONS

Published sales material entitled "RX-IP" to Atago Co. Ltd., 6 pages, obtained by Applicants' representatives no later than Jul. 23, 2002.
Published sales material entitled "RX-5000" to Atago Co. Ltd., 4 pages, obtained by Applicants' representatives no later than Jul. 23, 2002.
Published sales material entitled "Palette" to Atago Co. Ltd., 4 pages, obtained by Applicants' representatives no later than Jul. 23, 2002.
Published sales material entitled "Palette Digital Refractometer PR-32" to Atago Co. Ltd., 2 pages, obtained by Applicants' representatives no later than Jul. 23, 2002.
Published sales material entitled "UG-1" to Atago Co., Ltd., 2 pages, obtained by Applicants' representatives no later than Jul. 23, 2002.
Published sales material entitled "Refractometer DBX-50" to Atago Co., Ltd., 4 pages, obtained by Applicants' representatives no later than Jul. 23, 2002.
"Beverage Japan", vol. 3, No. 5, published in December, 1980.
"Atago RX-1" Service Manual, obtained by Applicants' representatives no later than Jul. 23, 2002.
"Atago DBX-50" Service Manual, obtained by Applicants' representatives no later than Jul. 23, 2002.
Operations Instruction Manual for Atago DBX-50 Digital Refractometer, obtained by Applicants' representatives no later than Jul. 23, 2002.
"Markson, Marson Science Inc.", 1980 Markson Catalog, obtained by Applicants' representatives no later than Jul. 23, 2002.
Published material entitled "Digital Refractometer DBX-55A", 2 pages, obtained by Applicants' representatives no later than Jul. 23, 2002.
"Automatic Digital Refractometer", downloaded from the internet at www.atago.net/english/product/digital_bottom/html no later than Dec. 2002.
"Atago Digital Refractometers, Model RX-5000α" Brochure ("VeeGee Scientific"), obtained by Applicants' representatives no later than Dec. 2002.
English language Abstract of JP 2003-215035.
English language Abstract of JP 8-114547.
English language Abstract of JP 11-295214.
English language Abstract of JP 2000-19110.
English language Abstract of JP 64-38634.
English language Abstract of JP 5-172632.
English language Abstract of JP 6-323990.
English language Abstract of FR 2578978.
English language Abstract of DE 19910301.
English language Abstract of JP 2003-057178.
English language Abstract of JP 1-202642.
English language Abstract of JP 63-033645.
English language Abstract of JP 9-281000.
English language Abstract of JP 2001-074647 A.
English language Abstract of JP 2001-200838 A.
English language Abstract of JP 2001-242079 A.

* cited by examiner

REFRACTOMETER

CROSS-REFERENCE TO RELATED APPLICATIONS

This application claims benefit of priority to Japanese Patent Application No. 2002-315814 filed on Oct. 30, 2002, the entire contents of which are incorporated by reference herein.

BACKGROUND OF THE INVENTION

1. Field of the Invention

This invention relates to a refractometer used for measuring sugar concentration or density in a solution.

2. Description of Relevant Art

Refractometers used to measure sugar concentration or density in a solution by directing light on the boundary interface of a sample and a prism then detecting light reflected at the interface using a photoelectric sensor and measuring refractive index (sugar concentration or density) in the sample from the signal output by the photoelectric sensor are well-known. Measurements conducted using a refractometer operate on the principle that the critical angle of incidence at which total reflection occurs at the interface of a prism and a sample is dependent on refractive index of the sample.

A refractometer according to the prior art as disclosed in examined utility model application publication No. Hei 3-26443, generally comprises an optical system as shown in FIG. 1. In other words, between a prism 102 and a light source 104 is installed a condenser lens 106 for focusing light from the light source 104. Further, an objective lens 110 that focuses a beam output from the prism 102 over the photoelectric sensor 108 is installed between the prism 102 and a photoelectric sensor 108 to obtain a boundary position having a clear light/shade contrast.

There is a problem however as such optical systems require a plurality of optical elements and therefore incur high production costs. Further the elements used for construction that contain the optical elements must be arranged separately with respect to each other and therefore require very accurate positioning further contributing toward high production costs.

Normally, a refractometer is installed with a sample stage 114 surrounding the interface surface 112 that forms the interface between the prism 102 and a sample S. The sample stage 114 comes into contact with a variety of different sample materials that may be disposed thereon such as foods, chemicals, fats and oils, high molecular compounds and the like and is therefore made of a metal such as stainless steel that is highly resistant to corrosion.

After a measurement is performed the interface surface 112 and sample stage 114 to which the sample S has been applied must be wiped completely clean to ensure that none of the material from the previous sample remains to contaminate the next measurement. It is difficult to remove the sample material applied to the sample stage of a refractometer according to the prior art however, when the sample measured is a paste like substance such as starchy syrup or the like. Wiping away previous sample material takes time causing a problem of reducing the efficiency of measuring operations. Further, when the wiping action to remove sample material is repeated many times the sample stage 114 easily suffers abrasions.

A problem affecting refractometers used to measure highly corrosive sample substances such as battery fluid or the like is that the sample stage 114 has a very short usable life. Further, if a sample such as an adhesive or the like that adheres strongly to the sample stage 114 is used it may not be possible to strip the sample material away thereby rendering further measurements impossible.

A refractometer operates on the premise that only reflected light of the interface surface 112 enters the photoelectric sensor 108, however a refractometer is not restricted to being used only indoors. When measuring samples such as a juice extract from a fruit or vegetable or antifreeze solution used in an automobile for example, the refractometer may frequently be used outdoors. In these situations external light rays that are changeable in space and time transmit the prism 102 from the direction of the sample itself and enter the photoelectric sensor 108. Thus, another problem affecting refractometers is that refractive index cannot be accurately measured in outdoor environments.

In order to enable refractive index to be accurately measured when outdoors, the user may use their hand as a cover from above the sample S or block the external light rays by using a cover, however when taking a measurement, using a hand as a cover or opening and closing a cover is troublesome and prevents measurements from being performed efficiently.

SUMMARY OF THE INVENTION

In order to solve the above-mentioned problems affecting conventional refractometers an object of the present invention is to provide a refractometer that has reduced production costs.

A further object of the present invention is to provide a refractometer that measures more efficiently and that can be used to measure all kinds of sample substances.

Yet another object of the present invention is to provide a refractometer that can accurately and efficiently measure refractive index even in outdoor environments.

In order to realize the above objects, according to a first aspect of this invention a refractometer for measuring refractive index of a sample is provided, this refractometer comprising a prism having an interface surface contacting the sample, a light source for radiating light so that the light enters the prism through an entrance face of the prism and strikes the interface surface, and an photoelectric sensor for receiving light reflected at the interface and entered from the prism through an exit face of the prism, wherein the light source and the photoelectric sensor are attached to entrance face and exit face of the prism, respectively.

According to another aspect of this invention a refractometer is provided comprising a prism having an interface surface providing the interface with a sample, and a sample stage arranged surrounding the interface surface, wherein the sample stage includes a non-adhesive coating formed.

According to yet another aspect of this invention a refractometer is provided in which light is radiated from a light source to an interface surface of a prism providing the interface with a sample, light reflected at the interface surface is detected using a photoelectric sensor to measure refractive index of the sample on the basis of the signal output from the photoelectric sensor, comprising filter means arranged between the interface surface and the photoelectric sensor, wherein the filter means includes a wavelength filter that selectively allows transmission of light having a wavelength within a prescribed region, including a wavelength of light of the light source.

According to yet another aspect of this invention a refractometer is provided comprising a prism having an interface surface providing the interface with a sample, a light source that radiates light towards the interface surface, a photoelectric sensor that receives light reflected at the interface surface, means for comparing luminous energy (luminous energy comparing means) that compares luminous energy measured by the photoelectric sensor when the light source is not lighting with a tolerance value set in advance, display means for displaying an error when the value for luminous energy measured when the light source is not lighting is greater than the tolerance value, means for lighting the light source when the value for luminous energy measured when the light source is not lighting is less than the tolerance value, and means for calculating refractive index (refractive index calculating means) for calculating refractive index from luminous energy distribution as measured by the photoelectric sensor when the light source is in a lit condition.

According to yet another aspect of this invention a method is provided for calculating refractive index using a refractometer comprising a prism having an interface surface providing the interface with a sample, a light source that radiates light towards the interface surface and a photoelectric sensor that receives light reflected at the interface surface, this method comprising the steps of measuring the luminous energy distribution by the photoelectric sensor when the light source is not lighting, comparing the luminous energy measured when the light source is not lighting with a tolerance value set in advance, displaying an error when the value for luminous energy measured when the light source is not lighting is greater than the tolerance value, measuring the luminous energy distribution with the photoelectric sensor when the light source is lit, if the luminous energy measured when the light source is not lighting is less than a tolerance value and calculating refractive index from luminous energy distribution measured as the light source is in a lit condition.

BRIEF DESCRIPTION OF THE DRAWINGS

These and other objects, features and advantages will become clearer from the following description of the preferred embodiment, read in connection with the accompanying drawings in which.

DETAILED DESCRIPTION OF THE PREFERRED EMBODIMENTS

Figure 1:
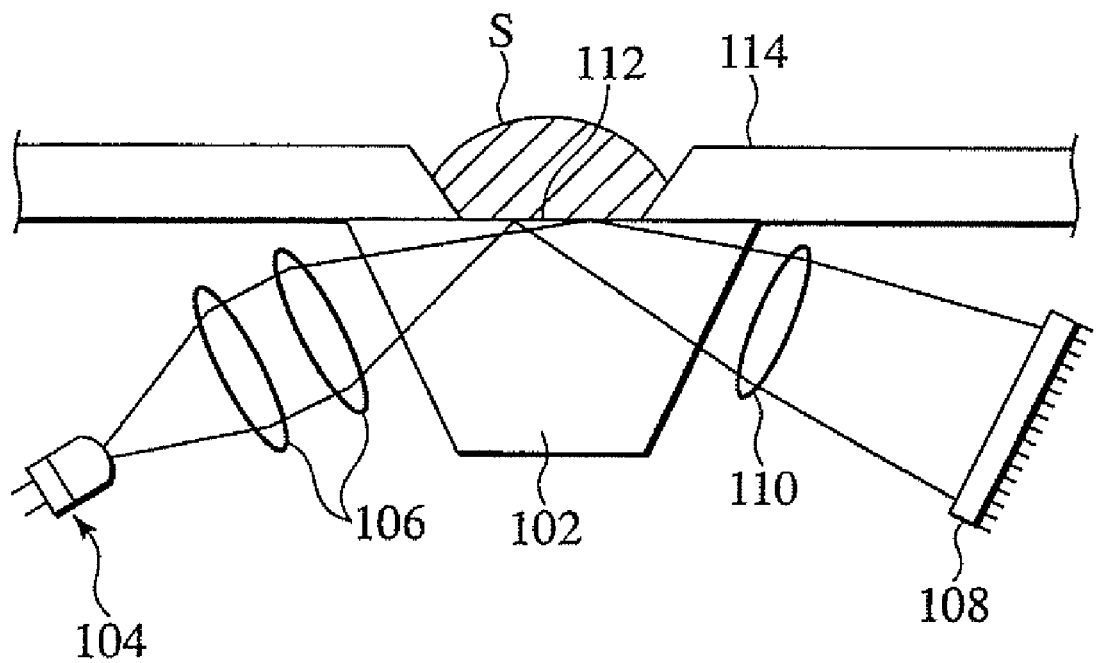
FIG. 1 is a cross-sectional view of a conventional refractometer.

The embodiments of this invention will now be described with reference to the drawings. The same or similar numbers are used in the drawings to represent the same or similar parts.

Figure 2:
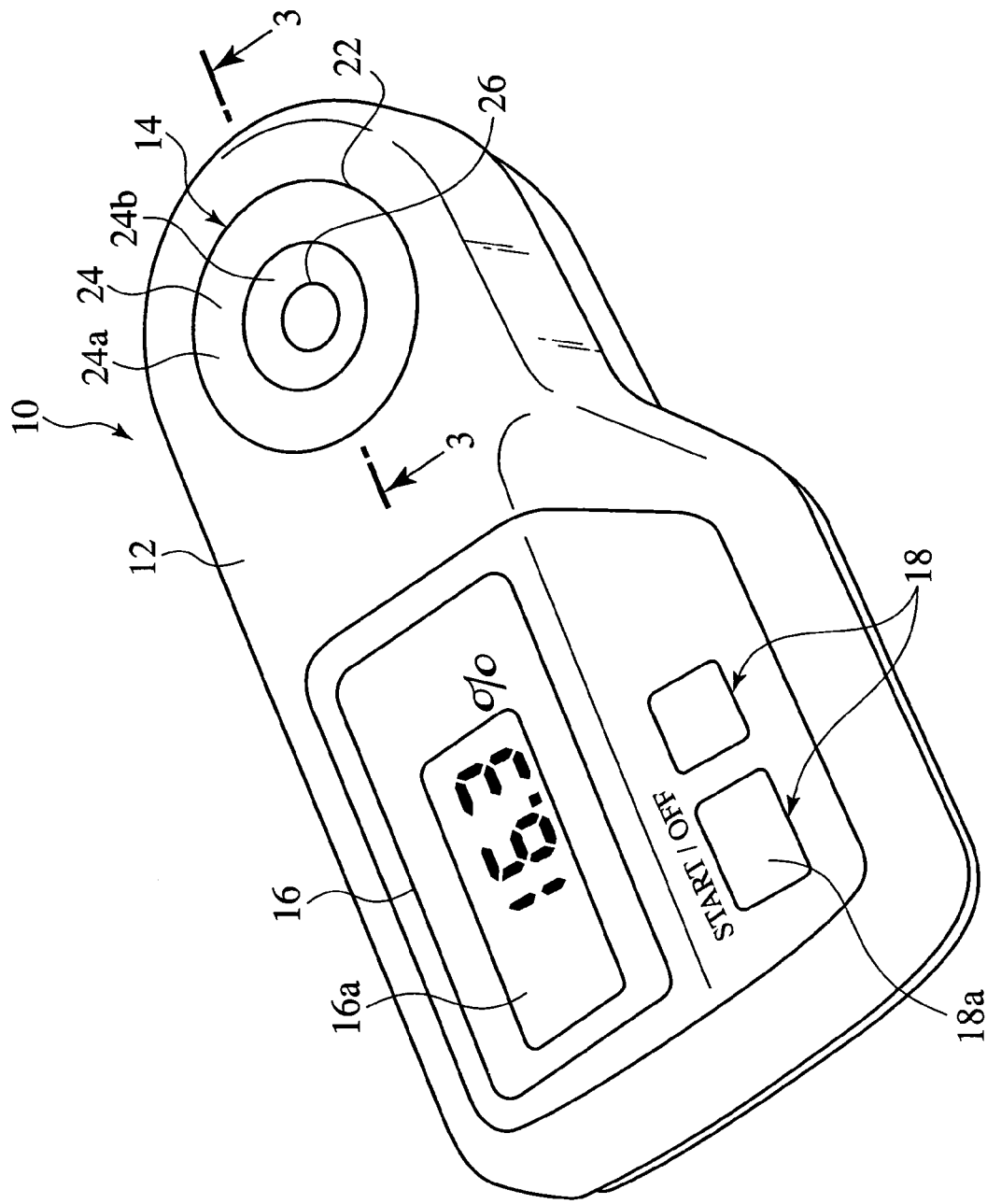
FIG. 2 is a perspective view of an embodiment of a refractometer according to the present invention.

FIG. 2 shows an embodiment of a refractometer according to the present invention. In this drawing a refractometer 10 includes a frame 12, a sample stage 14 onto which a sample is placed, a display part 16 for displaying sugar concentration or density in a sample and an operating part 18.

The frame 12 is normally of resinous material. A round opening 22 is installed in the upper part of the frame 12. The sample stage 14 is fitted in this opening 22, secured therein. The sample stage 14 comprises a sample guide face 24 exposed to the exterior and a round shaped opening 26 formed in roughly the center of the sample guide face 24. The sample guide face 24 comprises a flat face 24a abutting the peripheral fringe of the opening 22 and a conical face 24b extending inwards diagonally downwards from the flat face 24a towards the opening 26.

Figure 3:
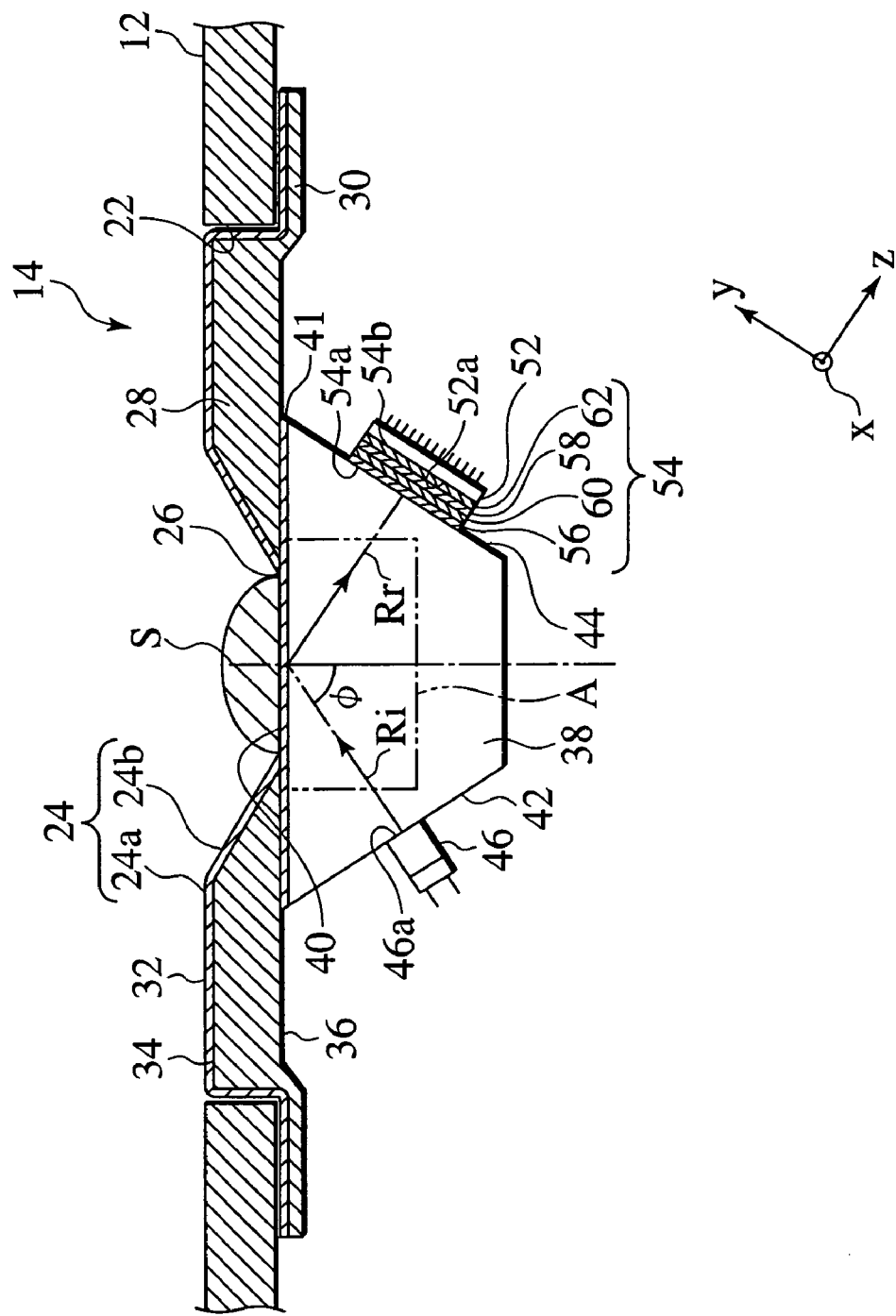
FIG. 3 is a cross-sectional view showing the major parts of the refractometer shown in FIG. 2.

FIG. 3 is a cross-sectional view of the sample stage 14 of the refractometer 10 shown in FIG. 2.

The sample stage 14 is generally disk shaped and comprises a thick center part 28 fitted embedded in the opening 22, and a thin peripheral part 30 extending from the center part 28 radially to the outside of the disk shape. The sample stage 14 is secured around the opening 22 by fastening means (not shown in the drawing) such as screws or the like in the peripheral part 30.

The sample stage 14 includes a non adhesive coating (plating) 34 formed over an upper face 32, encompassing also the sample guide face 24. This coating 34 includes metal and fine particles of fluorocarbon polymer evenly distributed within metal. More specifically, the coating 34 is a composite coating formed as a eutectoid combining particles of fluorocarbon polymer codeposited in metal. It is preferable for the thickness of the coating 34 to be approximately 3 to 5 μm.

The metal of this coating 34 includes chiefly nickel (Ni), and should preferably be a nickel phosphorus alloy including nickel and phosphorus. The fluorocarbon polymer of the coating 34 includes PTFE (polytetrafluoroethylene). It is preferable that the coating 34 includes 20-26 vol % fluorocarbon polymer and that the fluorocarbon polymer particles is 0.2-0.3 μm in diameter.

The coating 34 should be formed using electroless plating processes as this enables a coating of even thickness to be suitably adhered to the metal material such as stainless-steel or the like of the sample stage 14. Further, a harder coating can be obtained by applying heat treatment processes after the electroless plating processes are performed.

A coating 34 thus formed has the same non adhesive, water repellent, oil repellent and wear resistance (a low degree of friction) properties as fluorocarbon polymer. Further, such a coating has the same anticorrosive properties as a normal coating formed by electroless nickel plating. Thus, this coating 34 offers superior qualities in comparison to stainless-steel or the like used as the material for a conventional sample stage.

A prism 38 adheres to the lower face of the sample stage 14 filling the opening 26. As shown in FIG. 3 this prism 38 is trapezoid shaped viewed cross-sectionally and comprises a face 40 (lower face) exposed to the outside of the opening 26, a side face (entrance face) 42 into which light Ri from a light source 46 is radiated and a side face 44 (exit face) that directs reflected light Rr outward. The outwardly exposed face functions as the interface surface 40 that provides the interface with a sample S.

The interface surface 40 comprises the coating 41 including fluorocarbon polymer. It is preferable for this coating 41 to have the same non adhesive and corrosive resistance properties as the coating 34. Nanoclear coat made by Nikken Coating Industry Co., Ltd. located at 7-18-2 Arakawa, Arakawa-ku, Tokyo for example is suitable for this coating 41.

Because the non adhesive coating 34 is disposed on the sample stage 14 of this refractometer 10 it is difficult for sample S to become adhered to the sample stage 14. Likewise, it is also difficult for sample S to become adhered to the interface surface 40 as the non adhesive coating 41 is disposed on the interface surface 40. Accordingly sample S can be easily removed from the sample stage 14 and the interface surface 40 after a measurement of refractive index is performed. This reduces the time required to wipe away the sample S thereby improving the efficiency of measuring refractive index.

The superior anticorrosive properties of the coating 34 on the sample stage 14 extend the useful life of the sample stage 14 even when used to measure highly corrosive sample materials such as battery fluid or the like. Further, the non adhesive properties of the coating 34 on the sample stage 14 and the coating 41 on the interface surface 40 enable measurements to be performed of refractive index of samples of highly adhesive substances such as adhesive or the like that could not be performed with conventional refractometers.

Moreover, the water repellent and oil repellent properties of the coating 34 of the sample stage 14 ensure that a sample S dropped on the sample guide face 24 of the sample stage 14 is repelled down onto the interface surface 40 being easily collected together, maintained thereon. Accordingly when dropping a sample S to be measured, in comparison to a conventional refractometer it is not necessary to position the sample so definitively, thereby enabling refractive index measurements to be performed more easily.

Again, the superior wear resistance properties of the coating 34 of the sample stage 14 and the coating 41 of the interface surface 40 prevent the sample stage 14 and the interface surface 40 suffering abrasions as samples S are wiped away repeatedly. The fluorocarbon polymer particles are evenly dispersed within the coating 34, thus even if the coating 34 should incur some small abrasions, until the coating is completely exhausted above-described properties are maintained.

It is preferable for the light source 46 to be an LED (light emitting diode) that radiates light of a wavelength of approximately 589 nm. Again, the light source 46 may be a high intensity LED.

Hereafter, the plane defined by the light Ri that enters from the light source 46 to the interface surface 40 and the normal line N of the interface surface 40 (the plane parallel to the page of FIG. 3) is referred to a plane-of-incident A.

The light source 46 comprises a light emitting face 46*a* that is formed flat, and this flat light emitting face 46*a* adheres to an entrance face 42. Where a commercial light emitting diode is used for the light source 46 the light emitting face 46*a* can be formed by cutting through the top formed of a transparent resin and polishing the cut face thereof. The light source 46 directly abutting the prism 38 decreases luminous energy loss due to reflection at the entrance face 42 of incident light Ri.

On the side of the prism 38 having the exit face 44 is arranged filter means 54 for selecting the polarization and the wavelength for example of incident light, and a photoelectric sensor 52 (an photoelectric sensor) including a line sensor having a plurality of one dimensionally arranged light-receiving elements such as photodetectors.

Filter means 54 includes wavelength filter 56, 58 that selectively allows transmission of light having a wavelength within a prescribed region including wavelengths of light from the light source 46, a polarizer 60 that selectively allows transmission of light of a prescribed polarization, and a light (intensity) reducing filter 62 that reduces light intensity.

The wavelength filter 56, 58 further comprises a first wavelength filter 56 for selectively allowing transmission only of light of a comparatively short wavelength zone and a second wavelength filter 58 for selectively allowing transmission only of light of a comparatively long wavelength zone.

The first wavelength filter 56 blocks light the wavelengths of which are within the region from a predefined wavelength longer than wavelength of light from the light source 46 up to a maximum for wavelength as detected by the photoelectric sensor 52. For example, where the light source 46 is an LED with the center wavelength, 589 nm, the first wavelength filter 56 is a near-infrared cut filter or a heat ray cut filter that allows transmission only of shorter wavelengths, cutting out near-infrared light of approximately 700 nm or above. Specifically for example, a BG40 glass filter (a bandpass filter) made by Schott Corporation could be used for this first wavelength filter 56.

Figure 4:
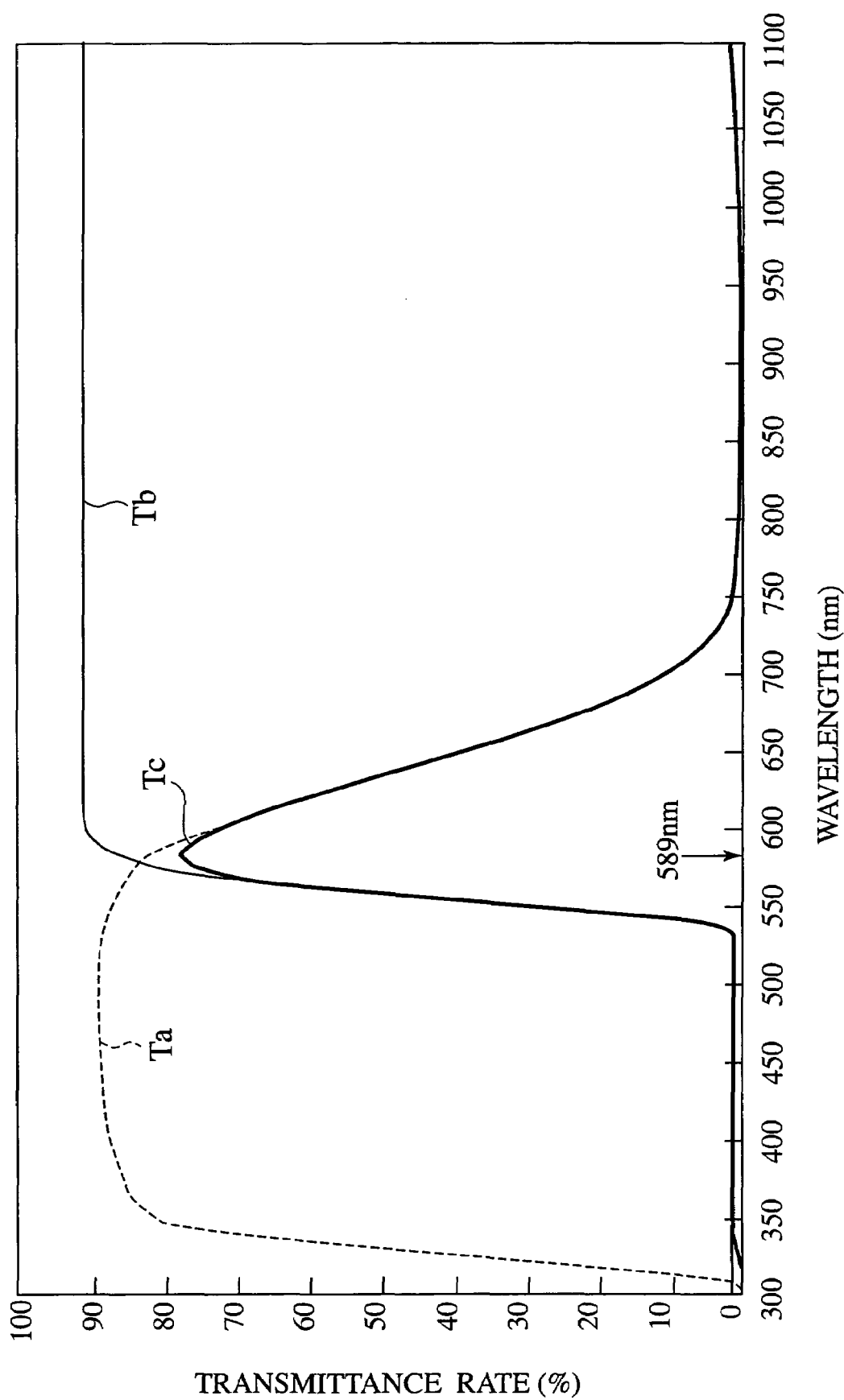
FIG. 4 shows light transmittance rates of light permitted to transmit by filter means of the refractometer shown in FIG. 2.

In FIG. 4 the curved line Ta shows the rate of light transmission using a BG40 filter of a thickness of 1.0 mm for a first wavelength filter 56. As shown in the drawing the first wavelength filter 56 allows transmission of greater than 70% of light of a short wavelength region from approximately 340 nm to 600 nm including light of the center wavelength of 589 nm from the light source 46. The wavelength filter 56 has half-maximum value at approximately 640 nm.

The second wavelength filter 58 blocks light the wavelengths of which are within the region from a predefined wavelength shorter than wavelength of light from the light source 46 to a minimum wavelength as detected by the photoelectric sensor 52. For example, where the light source 46 is an LED with the center wavelength, 589 nm, the second wavelength filter 58 is a filter that allows transmission only of longer wavelengths, cutting out visible range wavelengths and ultraviolet light of approximately 550 nm or below. Specifically for example, a sharp cut filter O-56 (JIS B7113 reference SO56) with a transmission limit wavelength of 560 nm (wavelength of the middle point of absorption limit wavelength at 5% transmittance and high transmission wavelength at 72% transmittance) can be used for this second wavelength filter 58.

In FIG. 4 the curved line Th shows the rate of light transmission using an O-56 filter of a thickness of 1.0 mm for a second wavelength filter 58. As shown in the drawing the second wavelength filter 58 allows transmission of greater than 70% of light of a long wavelength region from approximately 570 nm or greater, including light of the center wavelength of 589 nm from the light source 46. The wavelength filter 58 has half-maximum value at approximately 560 nm.

The curved line Tc in FIG. 4 shows the light transmission rate for the combination of the first wavelength filter 56 and the second wavelength filter 58. As shown in FIG. 4 the combination of the wavelength filter 56 and wavelength filter 58 allows transmission of greater than 70% of light of a wavelength region from approximately 570 nm to 600 nm. The combination of the wavelength filter 56 and wavelength filter 58 has half-maximum values at approximately 560 nm and 640 nm.

Again referring to FIG. 3, the polarizer 60 is arranged such that there is an axis of transmission in the plane-of-incident A, so as to block S-polarized light oscillating in a direction perpendicular to the plane-of-incident A and selectively allowing only P-polarized light to transmit. Transmission of only P-polarized light enables the greater part of incoming light from external sources to be blocked.

Light reducing (ND) filter 62 reduces the ratio of light in response to the brightness of light from the light source 46. Thus, as the light reducing filter 62 reduces the level of luminous intensity of light illuminated from the light source 46 to a level that is appropriate for the luminous intensity received by the photoelectric sensor 52, the filter 62 simultaneously reduces the luminous intensity of external light rays. Accordingly, to the extent that the degree of brightness of light from the light source 46 is high, the rate of light decrease due to the operation of the light reducing filter 62 is high (the transmittance rate is low), thereby reducing the proportion of external light rays in light penetrating through the light reducing filter 62 and entering into the photoelectric sensor 52.

As shown in FIG. 3, it is preferable for filter means 54 to form one integrated body in which the wavelength filters 56 and 58, the polarizer 60 and the light reducing filter 62 are laminated to each other. Further, it is preferable for a first face 54a of the filter means 54 to be adhered to the exit face 44 of the prism 38 and a light receiving face 52a of the photoelectric sensor 52 to be adhered to a second face 54b of the filter means 54. This enables filter means 54 and the photoelectric sensor 52 to be easily positioned in relation to the prism 38, secured thereto. As the photoelectric sensor 52 adheres to the prism 38 via filter means 54 loss of luminous energy through reflection of reflected light Rr at the exit face 44 and the light receiving face 52a of the photoelectric sensor 52 is reduced.

In this example, each of the filters 56, 58, 60 and 62 of filter means 54 are arranged such that reflected light from the interface surface 40 transmits in succession through the first wavelength filter 56, the polarizer 60, the second wavelength filter 58 and the light reducing filter 62, however, naturally, the order in which these filters 56, 58, 60 and 62 are arranged is of no consequence.

Omission of a condenser lens between the light source 46 and the prism 38 and omission of an objective lens between the prism 38 and the photoelectric sensor 52 in the above description enables a reduction in the size of the structure of the refractometer and a reduction in production costs.

The refractometer 10 can be easily constructed by first producing an optical system unit including the light source 46, the prism 38 and the photoelectric sensor 52 and then installing this unit in the frame 12. Further, because the positioning of the light source 46, the photoelectric sensor 52 and the prism 38 is performed prior to securing the prism 38 in the frame 12, this refractometer is more simple to produce than a conventional refractometer. This is a further factor enabling reduced production costs.

Operations in the region of the prism 38 of the refractometer 10 will now be described with reference to FIG. 3.

As a sample S is dropped on to the interface surface 40 the light source 46 lights up and light Ri from the light source 46 radiates into the interface surface 40. At an angle of incidence φ less than a critical angle of incidence φc(n) determined in response to refractive index n of the sample S, the greater part of the radiated light rays Ri transmit on the side having the sample S, while at an angle of incidence φ greater than the critical angle φc(n) the light rays Ri are reflected to the side having the photoelectric sensor 52.

Light rays Rr reflected at the interface surface 40 enter filter means 54. Filter means 54 operates such that only P polarized light oscillating parallel to the plane-of-incident A that is moreover, in a prescribed wavelength region (for example 550 nm-600 nm) including a wavelength of the light source 46, transmit to the side having the photoelectric sensor 52. Further the luminous intensity of light passing through filter means 54 is reduced to within a scope appropriate for luminous intensity received by the photoelectric sensor 52.

Reflected light from the light source 46 is comprised primarily of a wavelength of approximately 589 nm while incoming light from external sources includes wavelengths of the entire spectrum from infrared through to ultraviolet. Accordingly, as due to the operation of filter means 54 only light having a wavelength of approximately 589 nm is allowed to transmit, the greater part of incoming light from external sources is blocked, moreover the greater part of reflected light from the light source 46 is allowed to transmit to the photoelectric sensor 52. Again, the filter 54 operates such that only P-polarized light is allowed to transmit and as the luminous energy of transmitting light is reduced the ratio of external light to light entering into the photoelectric sensor 52 can be further reduced. Accordingly even when external light is extremely strong measurements can be performed without exceeding the dynamic range of the photoelectric sensor 52.

Using the refractometer 10 of the above described configuration, based on the luminous energy distribution curve measured by the photoelectric sensor 52, the critical angle point Pc (a position over the photoelectric sensor correspondent to the critical angle) correspondent to refractive index (sugar concentration, density) of the sample S, is calculated according to the following method.

Firstly, the range of the luminous energy distribution curve used to calculate the critical angle point Pc is decided. This is the range of addresses from a predetermined number (for example 30 points) of data approximating the locations (addresses) representing the maximum differential values for the luminous energy distribution curve. Alternatively, where there is a very limited range of measurements of refractive index by the refractometer 10, a range of addresses decided in advance with reference to the range of that refractive index can be used.

Next, data of m points in the range is used and the barycentric position Pc' is calculated through the expression $$P'_c = \frac{\sum_{i=1}^{m}\{(I_{i+1} - I_i) \times X_i\}}{\sum_{i=1}^{m}(I_{i+1} - I_i)} \quad (1)$$

In the expression (1), Xi shows the positions (addresses) of each light-receiving element and Ii shows received luminous energy (V) at Xi. It can be understood from applying expression (1) that barycentric position Pc' is the barycentric position of the first differential curve (or the first derivative curve) of the luminous energy distribution curve.

Finally a constant C is added to this barycentric position Pc' and critical angle point Pc (=Pc'+C) is calculated. The constant C is a value determined in advance by experiments using a sample refractive index of which is already known.

Here, where the luminous energy distribution curve includes significant external light, the shape of the luminous energy distribution curve and the first differential curve in the region of light transmission changes concomitant with changes in space and time of the external light, leading to substantial fluctuations for each measurement of barycentric position Pc' in relation to the true critical angle point. Accordingly it is not possible to accurately obtain the critical angle point Pc and refractive index.

Using this embodiment of a refractometer according to this invention a luminous energy distribution curve is obtained wherein due to the operation of filter means 54, external light is largely not included, thus enabling a stable barycentric position Pc' to be obtained. Accordingly, using the above described method the critical angle point Pc can be accurately obtained and refractive index can be accurately measured.

Calculation of the critical angle point Pc can also be performed using a second differential of the luminous energy distribution curve or both a first differential and a second differential.

Figure 5:
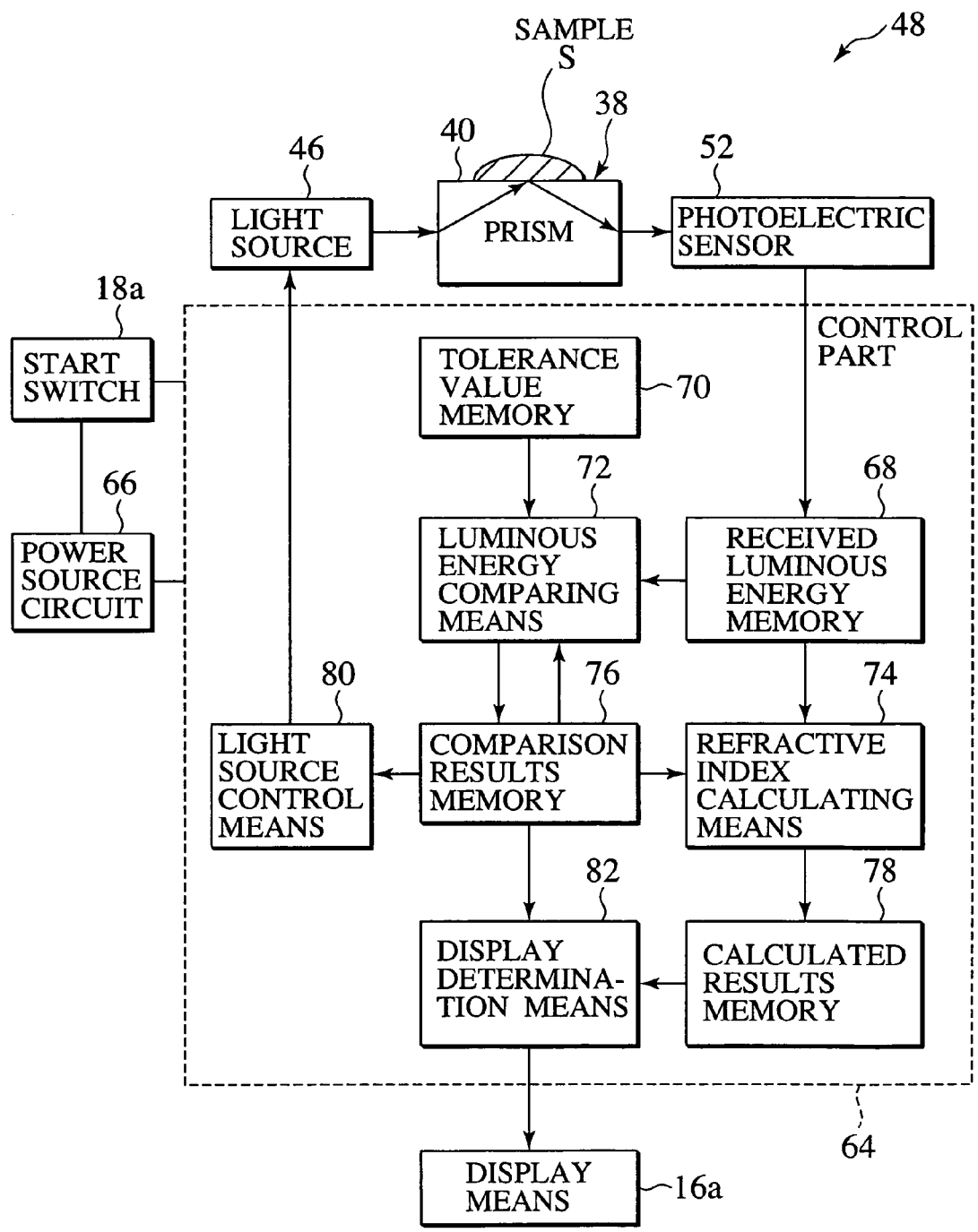
FIG. 5 is a block diagram schematically depicting the major parts of the refractometer shown in FIG. 2.

FIG. 5 is a block diagram schematically depicting the refractive index detection part 48 of the refractometer 10. As shown in the drawing the refractive index detection part 48 comprises a control part 64 connected to the light source 46 and the photoelectric sensor 52, display means 16a connected to the control part 64 as well as a start switch 18a and a power source circuit 66. The control part 64 comprises a received luminous energy memory 68, a tolerance value memory 70, luminous energy comparing means 72, refractive index calculating means 74, a comparison results memory 76, a calculated results memory 78, light source control means 80 and display determination means 82.

The received luminous energy memory 68 stores information on the luminous energy received by each light-receiving element of the photoelectric sensor 52. More specifically, received luminous energy output as an electric current signal from the photoelectric sensor 52 is converted into a digital signal after conversion to a voltage signal performed by an I-V converter (not shown in the drawing) or the like, and then stored in the received luminous energy memory 68.

The tolerance value memory 70 stores the tolerance value for incoming luminous energy from external sources (external light). These tolerance value are determined from experiments ensuring that errors in refractive index due to the effects of external light are within a predetermined range.

The comparison results memory 76 stores a value [N=0] or [N=1] indicating whether or not luminous energy entering from external sources is less than the tolerance value. [N=0] indicates that the value for luminous energy entering from external sources is greater than the tolerance value and [N=1] indicates that such value is less than the tolerance value. Initially the value for N is set as 0.

When [N=0], luminous energy comparing means 72 compares the luminous energy entering each light-receiving element (each position address) of the photoelectric sensor 52 as stored in the received luminous energy memory 68 with the tolerance value stored in the tolerance value memory 70. If luminous energy comparing means 72 decides that this luminous energy entering from external sources is greater than the tolerance value, means 72 maintains the initial value [N=0] in the comparison results memory 76. If luminous energy entering from external sources is less than the tolerance value, luminous energy comparing means 72 changes the value stored in comparison results memory 76 to [N=1].

Light source control means 80 causes the light source 46 to light if the value stored in comparison results memory 76 is changed to [N=1].

When [N=1], refractive index calculating means 74 uses the expression (1) of the above described method to calculate critical angle point Pc based on the distribution of luminous energy (luminous energy distribution curve) entering each light-receiving element of the photoelectric sensor 52 as stored in received luminous energy memory 68, and obtains from the critical angle Pc refractive index of the sample S and the sugar concentration or density.

The calculated results memory 78 stores refractive index and the sugar concentration or density as calculated by refractive index calculating means 74.

Based on the value N stored in the comparison results memory 76, display determination means 82 causes display means 16a to display "External light error" indicating luminous energy entering from external sources (external light) is excessive, or causes display means 16a to display the density or sugar concentration as stored in the calculated results memory 78. Where the value in the comparison results memory 76 is [N=0] display determination means 82 causes display means 16a to display "External light error." Where the value in the comparison results memory 76 is [N=1] display determination means 82 causes display means 16a to display the density or sugar concentration as stored in the calculated results memory 78.

Display means 16a is for example a segmented display type LCD (liquid crystal display) that displays the density or sugar content, or "External light error." Additionally, display means 16a displays errors including for example "Outside measurable range" when the density or sugar concentration exceeds the measurable range, "Error—measurement not possible" when the critical angle cannot be detected or "Temperature error" when the temperature is outside the range within which measurements can be performed. Means for displaying "External light error" can be provided separately from the means for displaying sugar concentration or density or means for displaying the other errors.

The operations of the control part 64 will now be described with reference to FIGS. 5 and 6.

Figure 6:
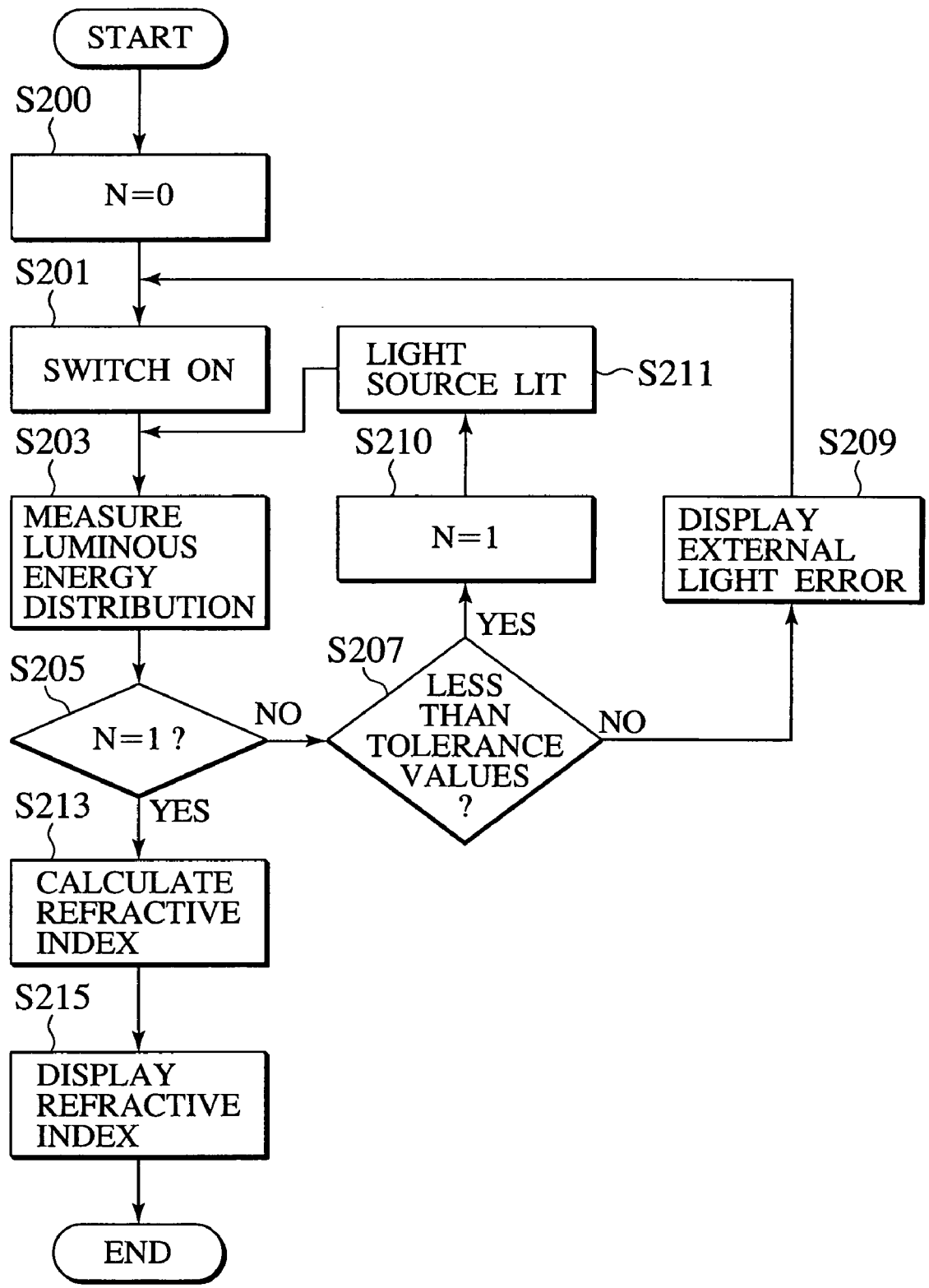
FIG. 6 is a flowchart showing the method for measuring refractive index used by the refractometer shown in FIG. 2.

FIG. 6 is a flowchart showing the method for measuring refractive index used by the refractometer 10.

At step S 200 the value in the comparison results memory 76 is set to the initial value, [N=0].

At step S 201 a sample S is set on the interface surface 40 by a user who then pushes the start switch 18a and turns the power source circuit 66 to ON.

At step S 203 the photoelectric sensor 52 measures luminous energy distribution and information on the luminous energy radiating into each of the light-receiving elements of the photoelectric sensor 52 is stored in the received luminous energy memory 68.

At step S 205, operations proceed to step S 207 because at the comparison results memory 76 [N=0].

At step S 207 luminous energy comparing means 72 compares luminous energy radiating into each of the light-receiving elements of the photoelectric sensor 52 as stored in the received luminous energy memory 68, to the tolerance value stored in the tolerance value memory 70. Here, because the light source 46 is not lighting, the only light radiating into each of these light-receiving elements is external light from external sources passing through the interface surface 40.

If, at step S 207, luminous energy entering any of these light-receiving elements is greater than the tolerance value, luminous energy comparing means 72 maintains [N=0] in the comparison results memory 76 and operations proceed to step S 209.

At step S 209 display determination means 82 causes display means 16a to display "External light error" based on the value [N=0] in the comparison results memory 76, and operations return to step S 201. Because "External light error" is displayed at display means 16a the user is made aware that refractive index cannot be measured as the external light is too strong and the user can then take appropriate action to block the external light such as covering the interface surface 40 by hand.

At step S 201 the user again presses the start switch 18a and at step S 203 the photoelectric sensor 52 measures luminous energy distribution and the measured results are stored in the received luminous energy memory 68. At step S 205, luminous energy comparing means 72 operates based on the value [N=0] in the comparison results memory 76 and operations proceed to step S 207.

At step S 207, where for example the user covers the interface surface 40 by hand such that luminous energy received by all of the light-receiving elements is less than the tolerance value, luminous energy comparing means 72 changes the value in the comparison results memory 76 to [N=1] at step S 210, and operations proceed to step S 211.

At step S 211 light source control means 80 lights the light source 46 based on the value [N=1] at the comparison results memory 76 and operations return to step S 203. At step S 203 luminous energy distribution is again measured by the photoelectric sensor 52, the measured result is then stored in the received luminous energy memory 68 and operations proceed to step S 205.

At step S 205 refractive index calculating means 74 operates based on [N=1] in the comparison results memory 76 and operations proceed to step S 213.

At step S 213 refractive index measuring means 74 calculates refractive index and the density or the sugar concentration based on the distribution of luminous energy radiating into each of the light-receiving elements of the photoelectric sensor 52 as stored in the received luminous energy memory 68. Because at step S 207 it was confirmed that the value for incoming luminous energy from external sources (external light) was less than the tolerance value, therefore light radiating into the light-receiving elements is chiefly light radiating from the light source 46 and reflected at the interface surface 40. Accordingly the critical angle point Pc can be accurately detected from this luminous energy distribution and the density or the sugar concentration can be accurately calculated. Refractive index and the density or sugar concentration thereby obtained is then stored in the calculated results memory 78.

At step S 215, based on the value [N=1] in the comparison results memory 76, display determination means 82 causes display means 16a to display the density or the sugar concentration as stored in the calculated results memory 78.

In the above described method of performing measurements, after "External light error" is displayed at step S 209, operations do not proceed to step S 203 until the start switch 18a is turned ON at step S 201, however the system can also proceed from step S 209 directly to step S 203. Thus, until there is confirmation that incoming luminous energy from external sources is less than tolerance value (N=1), the photoelectric sensor 52 can continue automatically repeating the measurements.

Next an actual example of measurements performed will be described with reference to FIGS. 7A and 7B.

Figure 7A:
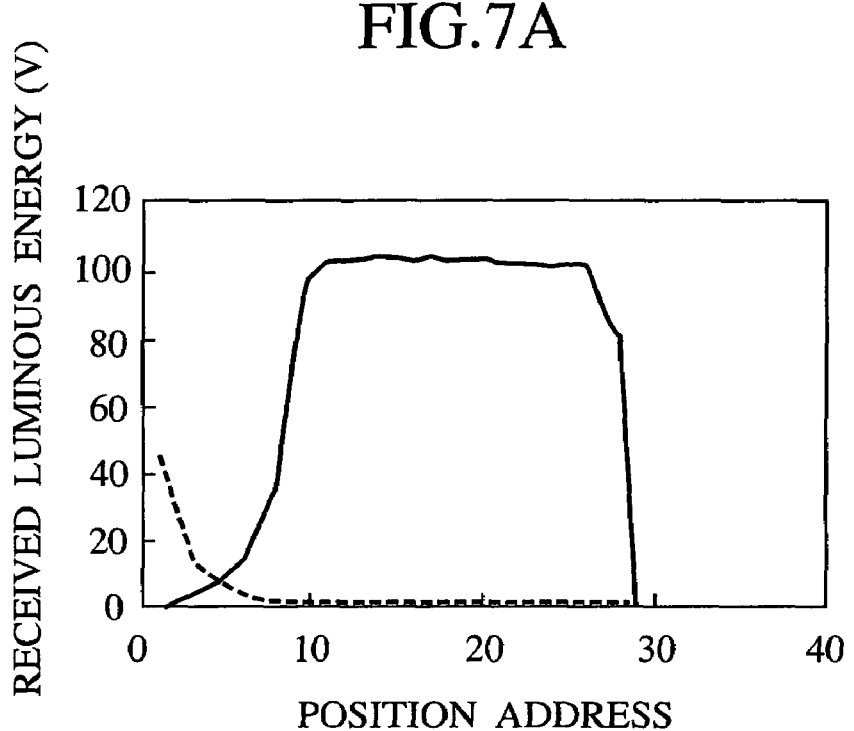
FIGS. 7A and 7B show luminous energy distribution measured using the refractometer of FIG. 2.
Figure 7B:
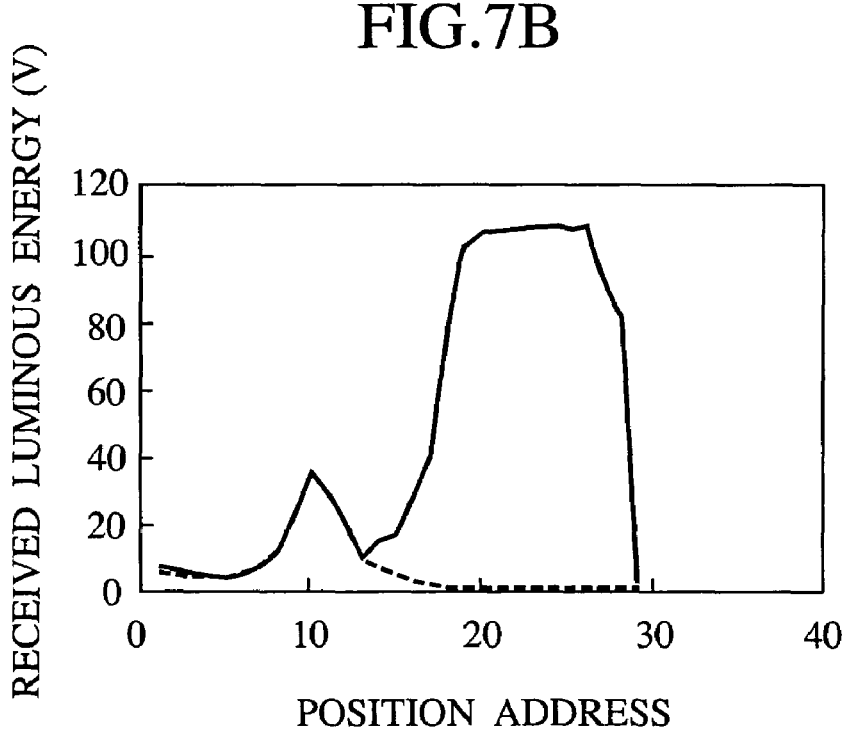

FIGS. 7A and 7B show luminous energy distribution measured using the refractometer 10. In FIGS. 7A and 7B the horizontal axis shows the position address of each light-receiving element of the photoelectric sensor 52 and the vertical axis shows the received luminous energy (V) of each light-receiving element.

The dotted lines in FIGS. 7A and 7B show luminous energy distribution as first measured at step S 203 shown in FIG. 6, when the light source 46 is not lighting. In other words these dotted lines show the distribution of incoming luminous energy from external sources. The solid lines in FIGS. 7A and 7B show luminous energy distribution measured at step S 203 when the light source 46 is in a lit condition. Here, the tolerance value for incoming luminous energy from external sources is set to 40V.

In the example of FIG. 7A, as shown by the dotted line, at the outset of the measurements it was determined at step S 207 that incoming luminous energy from external sources was greater than the tolerance value, therefore at step S 209 "External light error" is displayed.

As shown by the solid line, after the user took steps to block incoming light rays, measurement of the critical angle for total reflection was able to be performed from luminous energy distribution as measured with the light source 46 in a lit condition.

In the example of FIG. 7B, as shown by the dotted line, at the outset of the measurements it was determined at step S 207 that incoming light from external sources was less than the tolerance value 40 V. Accordingly "External light error" was not displayed and it was not necessary for the user to take any measures to block external light.

As shown by the solid line, luminous energy distribution measured under conditions where the light source 46 was in a lit condition and external light was not blocked out includes incoming light from external sources, however because the incoming light from external sources was less than the tolerance value, the critical angle for total reflection could be comparatively accurately measured from this luminous energy distribution also.

Accordingly the embodiment of the refractometer according to the present invention provides the following features.

1. A refractometer 10 for measuring refractive index of a sample S comprises:
   a prism 38 having an interface surface 40 contacting the sample S;
   a light source 46 for radiating light so that the light enters the prism through an entrance face 42 of the prism 38 and strikes the interface surface 40; and
   an photoelectric sensor 52 for receiving light reflected at the interface surface 40 and entered from the prism 38 through an exit face 44 of the prism 38,
   wherein the light source 46 and the photoelectric sensor 52 are attached to the entrance face 42 and the exit face 44 of the prism 38, respectively.
2. The light source 46 includes a flat light emitting face 46a, this flat light emitting face 46a being adhered to the entrance face 42 of the prism 38, the slit 50 intervening therebetween.
3. The photoelectric sensor 52 adheres to the exit face 44 of the prism.
4. The refractometer 10 has a slit 50 extending in the direction perpendicular to the plane-of-incidence, arranged between the light source 46 and the entrance face 42 of the prism 38.
5. A refractometer 10 comprises:
   a prism 38 having an interface surface 40 providing the interface with a sample S; and
   a sample stage 14 arranged surrounding the interface surface 40,
   the sample stage 14 includes a non-adhesive coating 34.
6. Material of the coating 34 includes metal and fine particles of fluorocarbon polymer evenly distributed therein.
7. The fluorocarbon polymer is polytetrafluoroethylene.
8. The coating material includes 20-26 vol % fluorocarbon polymer.
9. The diameter of the particles of the fluorocarbon polymer is 0.2-0.3 μm.
10. The interface surface 40 has a coating 41 including fluorocarbon polymer.
11. A refractometer 10 comprises:
    a frame having an opening therein;
    a prism 38 arranged in this opening and having an interface surface 40 that provides an interface with a sample S;
    a light source 46 that radiates light to the interface surface 40; and
    a sensor 52 for receiving light from the light source 46 reflected at the interface surface 40,
    the frame includes a sample guide face 24 provided at a perimeter of the opening and surrounding the interface surface 40, the sample guide face 24 includes a coating 34 including nickel and particles of fluorocarbon polymer evenly distributed therein, the fluorocarbon polymer is polytetrafluoroethylene, material of the coating 34 includes 20-26 vol % fluorocarbon polymer, the diameter of the particles of the fluorocarbon polymer is 0.2-0.3 μm, and the coating 34 is formed using electroless plating processes.

12. In a refractometer 10, light is radiated from a light source 46 to an interface surface 40 of a prism 38 providing the interface with a sample S, light reflected at the interface surface 40 is detected using a photoelectric sensor 52 to measure refractive index of the sample S on the basis of from a signal output from the photoelectric sensor 52, this refractometer comprises filter means 54 arranged between the interface surface 40 and the photoelectric sensor 52, the filter means 54 further includes wavelength filter 56 and 58 that selectively allow transmission of light having a wavelength within a prescribed region, including wavelengths of light of the light source 46.

13. The wavelength filter 56 and 58 includes a first wavelength filter 56 that selectively blocks light the wavelengths of which are within the region from a wavelength 50 nm longer than wavelength of light from the light source 46 up to a maximum wavelength as detected by the photoelectric sensor 52 and a second wavelength filter 58 that selectively blocks light the wavelengths of which are within the region from a wavelength 30 nm shorter than wavelength of light from the light source 46 to a minimum wavelength as detected by the photoelectric sensor 52.

14. The filter means 54 includes a polarizer 60 that selectively allows transmission of linearly polarized light.

15. The filter means 54 forms one integrated body, combining the wavelength filters 56 and 58 and the polarizer 60 laminated to each other.

16. The filter means 54 adheres to the prism 38 by a first face 54a and the photoelectric sensor 52 adheres to a second face 54b of the filter means 54.

17. The filter means 54 includes a light reducing filter 62.

18. A refractometer 10 comprises:

a prism 38 having an interface surface 40 that provides an interface with a sample S;

a light source 46 that radiates light to the interface surface 40;

a photoelectric sensor 52 for receiving light reflected at the interface surface 40;

luminous energy comparing means 72 that compares luminous energy measured by the photoelectric sensor 52 when the light source 46 is not lighting with a tolerance value set in advance;

display means 16a for displaying an error when the value for luminous energy measured when the light source 46 is not lighting is greater than the tolerance value, light source control means 80 for lighting the light source 46 when the value for luminous energy measured when the light source 46 is not lighting is less than the tolerance value, and refractive index calculating means 74 for calculating refractive index from luminous energy distribution as measured by the photoelectric sensor 52 when the light source 46 is in a lit condition.

19. The display means 16a displays refractive index as detected by refractive index calculating means 74.

20. A method for calculating refractive index using a refractometer 10 comprising a prism 38 having an interface surface 40 that provides an interface with a sample S, a light source 46 that radiates light to the interface surface 40 and a photoelectric sensor 52 for receiving light reflected at the interface surface 40, this method comprises:

a step 203 for measuring the luminous energy distribution using the photoelectric sensor 52 when the light source 46 is not lighting;

a step 207 for comparing the luminous energy measured when the light source 46 is not lighting with a tolerance value set in advance;

a step 209 for displaying an error when the value for luminous energy measured when the light source 46 is not lighting is greater than the tolerance value;

a steps 211 and 203 for lighting the light source 46 and measuring the luminous energy distribution using the photoelectric sensor 52, if the luminous energy measured when the light source 46 is not lighting is less than the tolerance value; and a step 213 for calculating refractive index from luminous energy distribution measured when the light source 46 is in a lit condition.

This refractometer provides the following effects.

(1) Omission of a condenser lens and an objective lens enables production costs to be reduced.

(2) Positioning of the light source, photoelectric sensor and prism is performed prior to installing the prism in the frame making the refractometer easy to produce and enabling production costs to be reduced.

(3) Loss of luminous energy can be reduced.

(4) The refractometer itself can be made smaller.

(5) A sample can be easily removed from over the sample stage and the interface surface.

(6) The time required to wipe away a sample is reduced thereby improving the efficiency of measuring refractive index.

(7) Refractive index can be measured of a sample that is a highly corrosive or highly adhesive substance.

(8) The sample stage and the interface surface do not easily suffer abrasion thereby extending the useful life of the refractometer.

(9) A sample can be easily and definitively maintained over the interface surface.

(10) The effects of external light, even in bright, outdoor places, are reduced enabling highly accurate refractive index measurements to be taken even outdoors.

(11) Refractive index measurements can be easily and efficiently performed.

The above description of the preferred embodiments according to the present invention is in all respects illustrative and not restrictive. Various other modifications will be apparent to and can be readily made by those skilled in the art without departing from the scope of the claims and spirit of this invention.

For example a first embodiment of this invention is described herein with reference to a desktop type refractometer however the invention of this application can be used in a variety of different refractometers such as a portable type or Abbe refractometer or the like.

Figure 8:
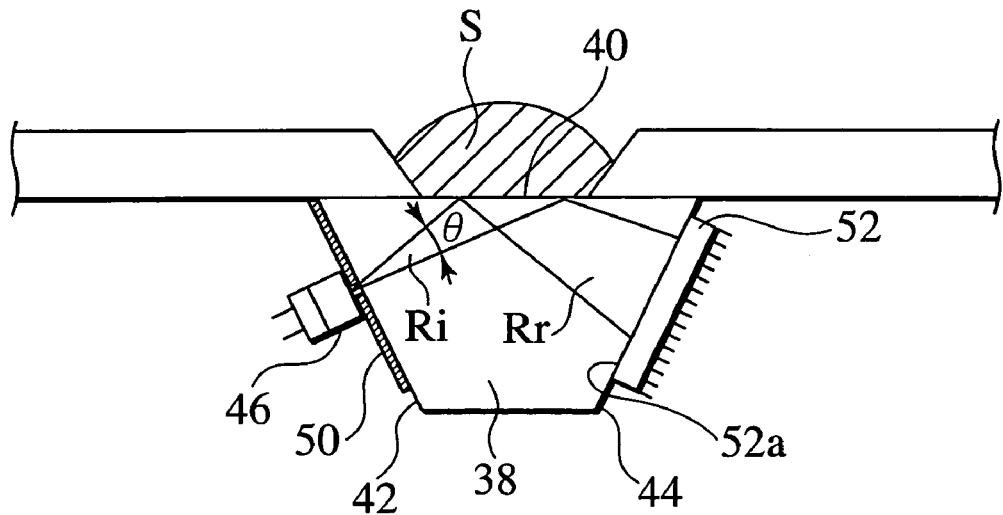
FIGS. 8 to 10 show other embodiments of a refractometer according to this invention.
Figure 9:
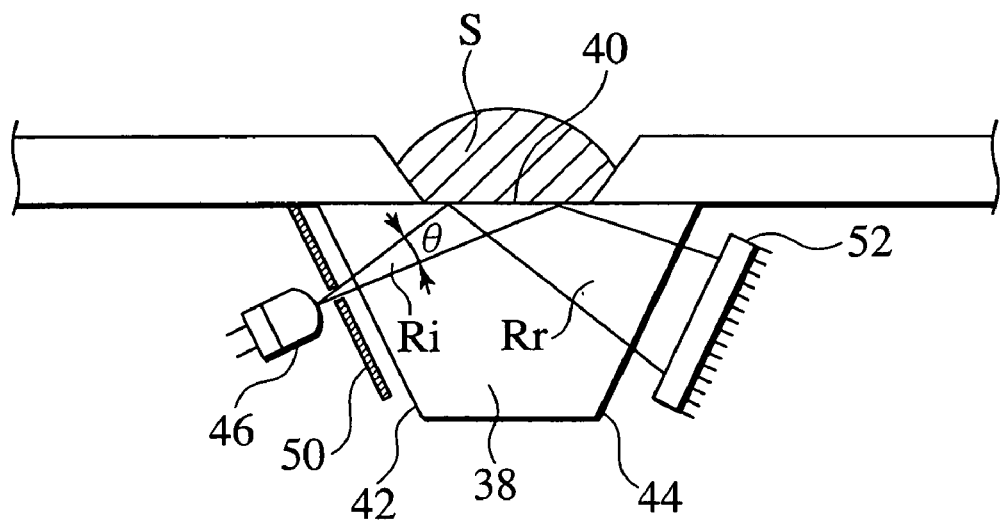

As shown in FIG. 8 the light source 46 can be adhered to the entrance face 42 in a configuration having a slit (or pinhole) 50 intervening therebetween. Alternatively, as shown in FIG. 9, the light source 46 and the entrance face 42 of the prism can be arranged apart with a slit 50 installed therebetween. The width of this slit 50 (or the diameter of the pinhole) should be for example 0.3 to 0.5 mm. This slit 50 acts such that the light Ri from the light source 46 is directed into the prism 38 at a comparatively small angle of diffusion θ. Thus, light of sufficient luminous energy can be irradiated to the desired region of the interface surface 40 without requiring installation of optical elements such as a condenser lens or the like operating on the optical path between the light source 46 and the prism 38. Moreover, without installing the optical elements such as a condenser lens or the like operating on the optical path between the prism 38 and the photoelectric sensor 52, reflected light Rr of sufficient luminous energy can be received in the desired region of the photoelectric sensor 52. Accordingly, as an objective lens and a condenser lens are omitted in the structure of the refractometer of this invention reduction costs can be reduced.

Figure 10:
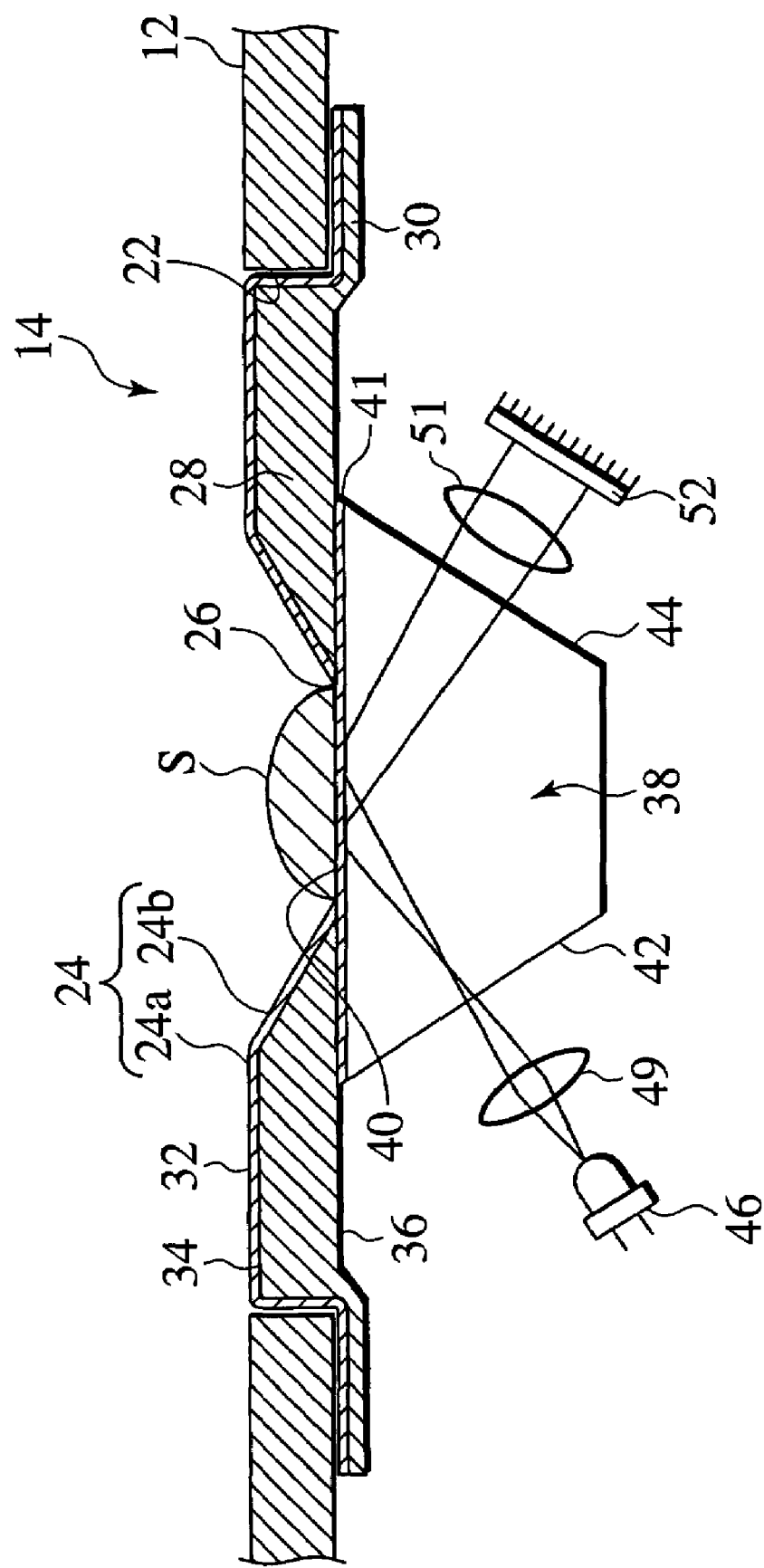

As shown in FIG. 10, the above described sample stage 14, filter means 54 and control means 64 can also be used in a refractometer having a condenser lens 49 and an objective lens 51.

Instead of the method for calculating the critical angle point Pc described above, a configuration wherein the critical angle point Pc is calculated based on the luminous energy distribution curve obtained after subtracting the luminous energy distribution curve measured when the light source 46 is not lit from the luminous energy distribution curve measured when the light source 46 is lit can also be used. This largely removes the influence of external light thereby enabling comparatively accurate refractive index measurements to be performed even in an extremely bright outdoor location.

EXPERIMENTAL EXAMPLE

In order to verify the effects of the coating 34 of the refractometer 10 according to the embodiments of this invention a refractometer 10 was produced for experimental purposes and subject to experiments designed to compare performance with a conventional refractometer.

A refractometer using a sample stage made from SUS316 was used as an example of prior art technology. For the experimental example a composite coating 34 was formed over the external face of a sample stage the same as that of the conventional refractometer. More specifically, the composition of the coating 34 of this experimental example comprised Ni: 82-84 wt %, P: 8-10 wt %, PTFE: 20-26 vol %. The diameter of the PTFE particles included in this coating 34 was 0.2-0.3 μm.

During the comparative experiment, each type of sample was dropped on to a cone shaped face 24b of a sample guide face 24 surrounding a interface surface 40 and a comparison was made of how well each of these samples slipped down over the interface surface 40 and the ease with which such samples could be wiped away. The samples used included water, sugar solutions having a concentration of 10%, 30% and 50%, milk, tomato ketchup, condensed milk, mayonnaise and dark honey. A Kimwipe towel was used to wipe away the sample substances.

The results of these experiments appear following.

Way in which sample slipped down:

When water was used as a sample applied using the conventional refractometer, the sample slipped down to the interface surface very well, however when the 10% sugar solution was used splashing droplets remained on the conical face. The 30% and 50% sugar solutions and the milk sample slipped down with some difficulty while the tomato ketchup, condensed milk, mayonnaise and dark honey samples had great difficulty slipping down to the interface surface.

In contrast to this, when the refractometer 10 produced for this experiment was used, the water sample and the sugar solutions with densities of 10%, 30% and 50% all slipped down very well. Further, the milk sample slipped down with some difficulty while the tomato ketchup, condensed milk, mayonnaise and dark honey samples had great difficulty slipping down to the interface surface.

Ease with which samples wiped away:

Using the conventional refractometer, the water and 10% sugar solution sample could be wiped away easily with 1 or 2 wipes however, when all of the other samples were used, it was easy for quantities of the sample substances to be left remaining even when wiping was performed with water added.

In contrast to this, using the refractometer 10 produced for this experiment, the water and the 10% sugar solution sample could be wiped away easily with 1 or 2 wipes and, when all of the other samples were used these could be wiped away more easily when water was added, than they could be wiped away using the conventional refractometer.

What is claimed is:

1. A refractometer for measuring refractive index of a sample, comprising:
   a prism having an interface surface for contacting said sample;
   a light source configured to radiate light so that the light enters the prism through an entrance face of said prism and irradiates said interface surface;
   a photoelectric sensor configured to measure a luminous energy distribution of light reflected from said interface surface through an exit face of said prism; and
   a slit extending in a direction parallel to said interface surface and said entrance face of said prism, the slit being arranged between said light source and said entrance face of said prism;
   wherein only said prism and said slit are provided in an optical oath between said light source and said photoelectric sensor, and
   wherein said light source and said photoelectric sensor are adjacent to said entrance face and exit face of said prism, respectively.

2. A refractometer according to claim 1, wherein said light source includes a flat light emitting face, said flat light emitting face being adhered to said entrance face of said prism.

3. A refractometer according to claim 1, wherein said photoelectric sensor adheres to said exit face of said prism.

4. A refractometer according to claim 1, further comprising:
   a slit extending in a direction perpendicular to a plane-of-incidence, the slit being arranged between said light source and said entrance face of said prism.

5. A refractometer, comprising:
   a frame having an opening;
   a prism arranged in said opening and having an interface surface, the interface surface being provable with a sample;
   a light source configured to radiate light to said interface surface; and
   a sensor configured to receive light reflected from said interface surface,
   wherein said frame includes a sample guide face provided at a perimeter of the opening and surrounding said interface surface,
   wherein said sample guide face includes a coating, the coating comprising a material including nickel and particles of fluorocarbon polymer evenly distributed, wherein said fluorocarbon polymer comprises polytetrafluoroethylene, wherein said material comprises approximately 20-26 vol % fluorocarbon polymer, wherein a diameter of said particles of said fluorocarbon polymer is approximately 0.2-0.3 μm, and wherein said coating is formed using electroless plating processes.

6. A refractometer, in which light is radiated from a light source to an interface surface of a prism, for measuring a refractive index of a sample provided on the interface surface of the prism, on a basis of a signal output from a photoelectric sensor that detects light reflected from said interface surface, the refractometer comprising:

a filter arranged between said interface surface and said photoelectric sensor, wherein said filter comprises:

a wavelength filter configured to selectively allow transmission of light having a wavelength within a prescribed region, including wavelengths of light of said light source; and a polarizer configured to selectively allow transmission of linearly polarized light, wherein said filter is formed as one integrated body, laminating said wavelength filter and said polarizer to each other.

7. A refractometer according to claim 6, wherein said wavelength filter comprises:

a first wavelength filter configured to selectively block light having wavelengths within a region ranging from a wavelength 50 nm longer than a wavelength of the light from said light source up to a maximum wavelength detectable by said photoelectric sensor; and a second wavelength filter configured to selectively block light having wavelengths within a region ranging from a wavelength 30 nm shorter than a wavelength of the light from said light source down to a minimum wavelength detectable by said photoelectric sensor.

8. A refractometer according to claim 6, wherein said filter comprises:

a first face that adheres to said prism; and a second face that adheres to said photoelectric sensor.

9. A refractometer according to claim 6, wherein said filter comprises a light reducing filter.

10. A refractometer, comprising:

a prism having an interface surface, the interface surface being provable with a sample;

a light source configured to radiate light to said interface surface;

a photoelectric sensor configured to receive light reflected from said interface surface;

a comparator configured to compare a luminous energy value measured by said photoelectric sensor when said light source is not radiating with a tolerance value;

a display configured to display an error when said luminous energy value is greater than said tolerance value;

a controller configured to control said light source to radiate light when said luminous energy value is less than said tolerance value; and a refractive index calculator configured to calculate a refractive index from a luminous energy distribution measured by said photoelectric sensor when said light source is radiating.

11. A refractometer according to claim 10, wherein said display displays said refractive index.

12. A method for calculating a refractive index using a refractometer comprising a prism having an interface surface, a light source that radiates light to the interface surface and a photoelectric sensor for receiving light reflected from the interface surface, the method comprising:

measuring a luminous energy distribution using the photoelectric sensor when the light source is not radiating;

comparing the measured luminous energy with a tolerance value;

displaying an error when the measured luminous energy is greater than the tolerance value;

controlling the light source to radiate light and measuring the luminous energy distribution using the photoelectric sensor when the measured luminous energy is less than the tolerance value; and calculating a refractive index from a luminous energy distribution measured when the light source is not radiating.

13. A refractometer for measuring a refractive index of a sample, comprising:

a prism having an interface surface adapted to contact said sample;

a light source configured to radiate light from an entrance face of said prism to said interface surface;

a photoelectric sensor configured to receive light reflected from said interface surface and directed outward from an exit face of said prism; and a slit extending in a direction parallel to said interface surface and said entrance face of said prism, the slit being arranged between said light source and said entrance face of said prism, wherein only said prism and said slit are provided in an optical path between said light source and said photoelectric sensor.

* * * * *

UNITED STATES PATENT AND TRADEMARK OFFICE
CERTIFICATE OF CORRECTION

| | | |
|---|---|---|
| PATENT NO. | : 7,492,447 B2 | Page 1 of 1 |
| APPLICATION NO. | : 10/693904 | |
| DATED | : February 17, 2009 | |
| INVENTOR(S) | : Yoshinori Nakajima et al. | |

It is certified that error appears in the above-identified patent and that said Letters Patent is hereby corrected as shown below:

Title Page, References Cited (56), Foreign Patent Documents, of the printed patent "8-114547 5/1976" should be --8-114547 5/1996--.

Signed and Sealed this

First Day of September, 2009

David J. Kappos
*Director of the United States Patent and Trademark Office*